United States Patent [19]
Bock et al.

[11] Patent Number: 4,758,336
[45] Date of Patent: Jul. 19, 1988

[54] DIALYTIC APPARATUS

[75] Inventors: Gerhard Bock, Friedewald; Michael Panse, Bad Homberg; Dieter Rath, Melsungen; Heinrich Eckel, Rotenburg; Rolf Heitmeier, Baunatal, all of Fed. Rep. of Germany

[73] Assignee: Intermedicat GmbH, Emmenbruecke, Switzerland

[21] Appl. No.: 940,927

[22] Filed: Dec. 12, 1986

[30] Foreign Application Priority Data

Jan. 14, 1986 [DE] Fed. Rep. of Germany ....... 3600793

[51] Int. Cl.$^4$ .............................................. B01D 13/00
[52] U.S. Cl. ................................. 210/90; 210/321.65; 604/5
[58] Field of Search ............... 210/321.3, 321.2, 321.1, 210/90, 85, 321.65; 604/4, 5, 6

[56] References Cited
U.S. PATENT DOCUMENTS 4,514,295 4/1985 Mathieu et al. .............. 210/321.3 X Primary Examiner—Frank Spear
Attorney, Agent, or Firm—Spensley Horn Jubas & Lubitz

[57] ABSTRACT

A dialytic apparatus for single-needle dialysis comprises a first pump in the artery conduit, which first pump in the first phase conveys blood from the patient into the expansion chamber while the vein conduit is shut off. At the same time, the second pump transports blood from the expansion chamber to the dialyzer. This regulation is performed in dependence from the pressure in the vein conduit so that the pressure decrease caused by ultrafiltration is counterbalanced. In the second phase, the first pump stands still and closes the artery conduit while the second pump conveys blood out of the expansion chamber to the dialyzer at a constant rate.

8 Claims, 1 Drawing Sheet

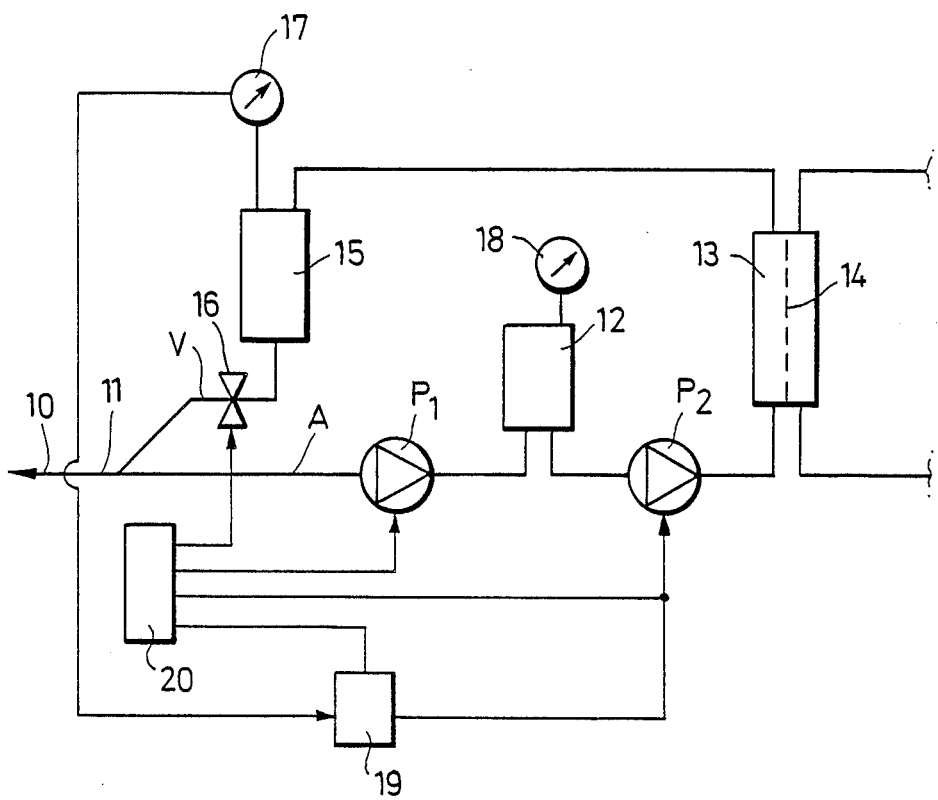

DIALYTIC APPARATUS

BACKGROUND OF THE INVENTION

1. Field of the Invention

The present invention relates to a dialytic apparatus for single-needle dialysis and in particular to a dialytic apparatus having an expansion chamber interposed between a first pump and a second pump in the artery conduit leading to the blood-inlet port of the dialyzer.

2. Description of Related Art

When a single-needle hemodialysis is performed, the patient is punctured by a single needle at a single spot. During a first phase, blood is taken away from the patient through this needle and conveyed to the dialyzer. During a second phase the blood is returned from the dialyzer to the patient.

A dialytic apparatus is known (German Patent Specification No. 22 36 433) which comprises a closed system in which the single one-bore needle is alternately connected to the artery branch and the vein branch while the respective other branch is shut off. During the first phase, the vein branch is closed. The pump conveys blood from the patient via the artery branch to the dialyzer. The first phase is finished when the pressure at the blood outlet port of the dialyzer has reached an upper limiting value. In the succeeding second phase, the artery conduit is shut off, and the vein conduit is opened. Subsequently, under the release of pressure, the blood flows back into the patient via the vein conduit and the needle. This known system is based on time-dependent variations of the pressures at the dialyzer, which variations are used for controlling the device. However, variations of pressure at the dialyzer membrane greatly disturb the function of the dialyzer itself, since the variations influence the ultrafiltration rate and prevent a balanced ultrafiltration through the dialyzer membrane. Additionally, if there is a standstill of the blood flow at the dialyzer membrane, the continuing ultrafiltration can cause a decrease of the vein return pressure below the permittd limiting value, so that a corresponding alarm device is actuated.

In a further known dialytic apparatus (U.S. Pat. No. 4,614,590), an expansion chamber is interposed in a parallel branch of a single pump. During the first phase, the pump conveys blood into the expansion chamber while the blood passage through the dialyzer is blocked. During the second phase, the pump conveys the blood out of the expansion chamber to the dialyzer, the artery conduit being shut off. Here again, there are considerably changes of the transmembrane pressure at the dialyzer membrane and an intermittently interrupted discontinuous dialysis. A lower limiting value of the vein return pressure cannot be easily maintained.

It is therefore an object of the present invention to provide a single needle dialytic apparatus in which the pressure exerted on the dialyzer membrane from the blood side is not subjected to large changes when the vein conduit is shut off.

SUMMARY OF THE INVENTION

In accordance with the present invention, these and other objectives are achieved by providing a second pump interposed between the expansion chamber and the blood-inlet port of the dialyzer, which second pump is driven when the artery conduit is open in such a manner so as to basically counterbalance the pressure decrease in the blocked vein conduit caused by the ultrafiltration.

In the dialytic apparatus according to the present invention, blood is further supplied to the dialyzer during the second phase; i.e., when the vein conduit is shut off, which blood supply is performed by the second pump while the first pump conveys blood from the needle to the expansion chamber. During this process, the second pump is driven in such a manner that it compensates the ultrafiltration rate of the dialyzer; i.e., that it substitutes the amount of fluid passing the dialyzer membrane. Thus, the blood side pressure on the dialyzer membrane is generally kept constant so that a balancing of the ultrafiltration is possible. This means that the ultrafiltration amount per unit time is basically constant. Further, the invention ensures that the vein return pressure is maintained at the required level. A possible rupture of a tube in a vein return conduit is unmistakably detected by the resulting pressure decrease.

According to a preferred further embodiment, the second pump is driven at a constant rate when the artery conduit is shut off. The second pump conveys the blood contained in the expansion chamber through the dialyzer at a constant rate. Thus, in this phase the blood conveyance is neither performed by the first pump nor by a release of pressure of the expansion chamber. By the steady operation of the second pump, the blood supply to the dialyzer is constant with respect to time in the second phase while the first pump stands still and the artery conduit is shut off.

Preferably, the driving speed of the second pump is controlled by a pressure sensor linked to the vein conduit, the output signal of the pressure sensor controlling the second pump when the vein conduit is closed. Further, the vein conduit may comprise an air trap, the air space of which is connected to the pressure sensor.

BRIEF DESCRIPTION OF THE DRAWING

A detailed description of the invention will be made with reference to the accompanying drawing.

FIG. 1 is a schematic diagram illustrating the various elements of a preferred embodiment of the present invention.

DESCRIPTION OF THE PREFERRED EMBODIMENT

The following detailed description is of the best presently contemplated mode of carrying out the invention. This description is not to be taken in a limiting sense, but is made merely for the purpose of illustrating the general principles of the invention. The scope of the invention is defined by the appended claims.

In the embodiment of the invention illustrated in FIG. 1, a one-bore needle 10, the point of which may be punctured into a blood vessel of the patient, is connected to a blood conduit 11. The blood conduit 11 branches into an artery conduit A and a vein conduit V. In the artery conduit A, there are arranged successively the pump P1, the expansion chamber 12, the pump P2 and the dialyzer 13. The membrane of the dialyzer is marked by reference numeral 14.

Vein conduit V contains the shut-off valve 16 and the air trap 15 and is connected to the blood-outlet port of dialyzer 13. Air trap 15 is a closed vessel from the upper end of which a pressure line leads to a pressure sensor 17. The pressure sensor may additionally be adapted as an indicating means.

Both pumps P1 and P2 are positive-displacement pumps, preferably peristaltic tube pumps. If pump P1 is inactive, it squeezes off the tube and thus acts as a shut-off device for artery conduit A. The shut-off device of vein conduit V is formed by shut-off valve 16.

When the dialytic apparatus is in operation, shut-off valve 16 is closed in the first phase, and the first pump P1 conveys blood from the patient into expansion chamber 12. The expansion chamber 12 is also a closed chamber. When the blood level in chamber 12 is rising, the air is either driven out of the chamber 12 or compressed. The pressure in the expansion chamber 12 may be indicated by a pressure gauge 18 and, if necessary, evaluated for controlling the apparatus. While blood is conveyed into expansion chamber 12, the second pump P2 pumps blood out of the expansion chamber and to the blood-inlet port of the dialyzer 13. The transfer rate of the second pump P2 is controlled by pressure sensor 17 emitting a signal to regulator 19 which regulates the speed of the second pump P2. Pump P2 supplies an amount of blood to the dialyzer 13 such that the loss of liquid caused by ultrafiltration is counterbalanced and the pressure in air trap 15 remains constant. The first phase is terminated when the pressure in the expansion chamber 12 reaches a given limiting value, or when the blood level reaches a given limiting value, or after a predetermined span of time has elapsed.

After the end of the first phase, the second phase is performed; i.e., the phase of returning the refined blood to the patient. In this phase, the first pump P1 is inactive and blocks artery conduit A while shut-off valve 16 of vein conduit V is open. The second pump P2 pumps blood out of expansion chamber 12 via dialyzer 13 to vein conduit V and to the patient. In this second phase, the driving force of pump P2 is preferably constant but may be changed. The second phase is finished when the blood level has sunk to a given lower limiting value, or when the pressure in expansion chamber 12 reaches a given lower limiting value, or after a predetermined span of time is over.

The described processes may be controlled by controller 20 which effects the switching of shut-off valve 16 and pump P1 as well as the actuation of pump P2 in the second phase. Further, controller 20 actuates only regulator 19 in the first phase, so that the latter can regulate the speed of pump P2 in order to maintain constant pressure in air trap 15 and the outlet port of the dialyzer, respectively.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A dialytic apparatus for single-needle dialysis, comprising:
   a needle for puncturing a blood vessel;
   a blood conduit connected to the needle and branching into an artery conduit and a vein conduit;
   a dialyzer connecting the artery conduit with the vein conduit;
   two shut-off devices in the artery conduit and the vein conduit which shutoff devices can be actuated alternately;
   a first pump in the artery conduit;
   an expansion chamber interposed between the outlet port of the first pump and the blood-inlet port of the dialyzer;
   a second pump interposed between the expansion chamber and the blood-inlet port of the dialyzer; and
   means for regulating the driving speed of said second pump based on the pressure level within the vein conduit in such a manner so as to generally counterbalance the pressure decrease in the shut-off vein conduit which is caused by ultrafiltration when the vein conduit is shut off and said first pump is running.

2. A dialytic apparatus according to claim 1, wherein the second pump is driven at a constant speed when the artery conduit is shut off.

3. A dialytic apparatus according to claim 1, further comprising a pressure sensor connected to the vein conduit, the output signal of the pressure sensor controlling the second pump when the vein conduit is shut off.

4. A dialytic apparatus according to claim 3, wherein the vein conduit comprises an air trap the air space of which is connected to the pressure sensor.

5. An apparatus for blood dialysis comprising:
   a needle through which blood may be transferred;
   a dialyzer having an inlet port and an outlet port;
   a dialyzer membrane associated with said dialyzer;
   an artery conduit for conveying blood from the needle to the dialyzer inlet port;
   a vein conduit for conveying blood from the dialyzer outlet port to the needle;
   a first shut-off valve interposed in the vein conduit for stopping the flow of blood through the vein conduit;
   an expansion chamber interposed in the artery conduit between the dialyzer inlet port and the needle;
   a first pump interposed in the artery conduit between the needle and the expansion chamber for conveying blood from the needle to the expansion chamber;
   a second pump interposed in the artery conduit between the expansion chamber and the dialyzer inlet port for conveying blood from the expansion chamber to the dialyzer inlet port; and
   means for regulating said second pump in response to pressure levels within said vein conduit,
   said second pump conveying blood to the dialyzer inlet port at a rate which minimizes variations of pressure at the dialyzer membrane when said first pump is running and said vein conduit is closed.

6. An apparatus as in claim 5 further comprising means for controlling the second pump so that the second pump conveys blood to the dialyzer inlet port at a constant rate when the second shut-off valve stops the flow of blood through the artery conduit.

7. An apparatus as in claim 5 further comprising a pressure sensor for measuring the pressure of blood in the vein conduit and producing an output signal in response thereto, whereby the output signal may be utilized to control the second pump when the first shut-off valve stops the flow of blood through the vein conduit.

8. An apparatus as in claim 7 further comprising an air trap interposed in the vein conduit between the dialyzer outlet port and the needle, said air trap including an air space therein, said pressure sensor being in communication with said air space.

* * * * *